United States Patent [19]

Urbach et al.

[11] Patent Number: 4,591,598

[45] Date of Patent: May 27, 1986

[54] DERIVATIVES OF 2-AZABICYCLO[3.1.0]HEXANE-3-CARBOXYLIC ACID, AND HYPOTENSIVE USE THEREOF

[75] Inventors: Hansjörg Urbach, Kronberg; Rainer Henning, Hattersheim am Main; Reinhard Becker, Wiesbaden, all of Fed. Rep. of Germany

[73] Assignee: Hoechst Aktiengesellschaft, Fed. Rep. of Germany

[21] Appl. No.: 627,639

[22] Filed: Jul. 3, 1984

[30] Foreign Application Priority Data

Jul. 6, 1983 [DE] Fed. Rep. of Germany ....... 3324263

[51] Int. Cl.[4] .................... C07D 209/02; A61K 31/40
[52] U.S. Cl. .................... 514/412; 548/348; 548/452; 548/455; 546/112; 546/216
[58] Field of Search .................. 548/452, 455; 514/412

[56] References Cited

U.S. PATENT DOCUMENTS 2,833,810  5/1958  Kissman ............... 260/471
4,056,623  11/1977  Duhault ............... 514/412
4,235,921  11/1980  Achius et al. ......... 514/412

FOREIGN PATENT DOCUMENTS 0131226  6/1984  European Pat. Off. ........... 514/412

OTHER PUBLICATIONS

Erlanger et al, Jacs, vol. 73, pp. 4025–4027 (1951).
Vincent et al, "Tetrahedron Letters", vol. 23, No. 16, pp. 1677–1680 (1982).

Primary Examiner—Glennon H. Hollrah
Assistant Examiner—D. B. Springer

Attorney, Agent, or Firm—Finnegan, Henderson, Farabow, Garrett & Dunner

[57] ABSTRACT

The invention relates to compounds of the formula I

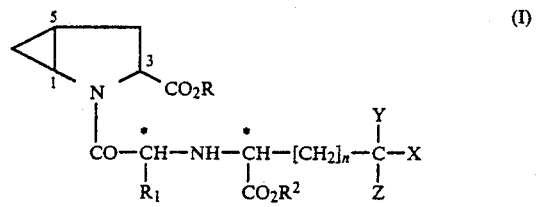

in which n denotes 0 or 1, R denotes hydrogen, alkyl, alkenyl or aralkyl, $R^1$ denotes hydrogen or alkyl, which can optionally be substituted by amino, acylamino or benzoylamino, alkenyl, cycloalkyl, cycloalkenyl, cycloalkylalkyl, aryl or partially hydrogenated aryl, each of which can be substituted by alkyl, alkoxy or halogen, aralkyl or aroylalkyl, both of which can be substituted in the aryl radical as defined previously, a monocyclic or bicyclic S- or O- and/or N-heterocyclic radical or a side chain of an aminoacid, $R^2$ denotes hydrogen, alkyl, alkenyl or aralkyl, Y denotes hydrogen or hydroxyl, Z denotes hydrogen, or Y and Z together denote oxygen, X denotes alkyl, alkenyl, cycloalkyl, aryl, which can be monosubstituted, disubstituted or trisubstituted by alkyl, alkoxy, hydroxyl, halogen, nitro, amino, acylamino, alkylamino, dialkylamino and/or methylenedioxy, or 3-indolyl, and to a process for their preparation, agents containing them and and their use, and to 2-azabicyclo[3.1.0]hexane derivatives as intermediates, and a process for their preparation.

11 Claims, No Drawings

DERIVATIVES OF 2-AZABICYCLO[3.1.0]HEXANE-3-CARBOXYLIC ACID, AND HYPOTENSIVE USE THEREOF

The invention relates to derivatives of 2-azabicyclo[3.1.0]hexane-3-carboxylic acid of the formula I

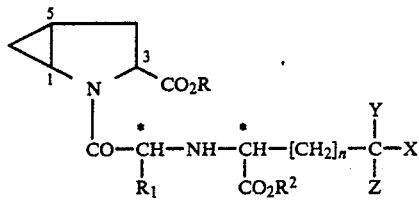

in which the hydrogen atoms at the bridgehead carbon atoms have the cis configuration with respect to one another, and the COOR group on carbon atom 3 is oriented exo or endo to the bicyclic ring system, and in which n denotes 0 or 1, R denotes hydrogen, $(C_1-C_6)$-alkyl, $(C_2-C_6)$-alkenyl or $(C_6-C_{12})$-aryl-$(C_1-C_4)$-alkyl, $R^1$ denotes hydrogen or ($C_1$ to $C_6$)-alkyl, which can optionally be substituted by amino ($C_1$ to $C_6$)-acylamino or benzoylamino, ($C_2$ to $C_6$)-alkenyl, ($C_5$ to $C_9$)-cycloalkyl, ($C_5$ to $C_9$)-cycloalkenyl, ($C_5$ to $C_7$)-cycloalkyl-($C_1$ to $C_4$)-alkyl, ($C_6$ to $C_{12}$)-aryl or partially hydrogenated ($C_6-C_{12}$)-aryl, each of which can be substituted by ($C_1$ to $C_4$)-alkyl, ($C_1$ or $C_2$)-alkoxy or halogen, ($C_6-C_{12}$)-aryl-($C_1$ to $C_4$)-alkyl or ($C_7-C_{13}$)-aroyl-($C_1-C_2$)-alkyl, both of which can be substituted in the aryl radical as defined above, a monocyclic or bicyclic heterocyclic radical having 5 to 7 or 8 to 10 ring atoms respectively, 1 or 2 of these ring atoms being sulfur or oxygen atoms and/or 1 to 4 of these ring atoms being nitrogen atoms, or an optionally protected side chain of a naturally occurring α-aminoacid $R^1$—CH(NH$_2$)—COOH, $R^2$ denotes hydrogen, $(C_1-C_6)$-alkyl, $(C_2-C_6)$-alkenyl or $(C_6-C_{12})$-aryl-$(C_1-C_4)$-alkyl, Y denotes hydrogen or hydroxyl, Z denotes hydrogen, or Y and Z together denote oxygen, and X denotes $(C_1-C_6)$-alkyl, $(C_2-C_6)$-alkenyl, $(C_5-C_9)$-cycloalkyl, $(C_6-C_{12})$-aryl, preferably phenyl, which can be monosubstituted, disubstituted or trisubstituted by $(C_1-C_4)$-alkyl, $(C_1-C_4)$-alkoxy, hydroxyl, halogen, nitro, amino, acylamino, $(C_1-C_4)$-alkylamino, di-$(C_1-C_4$-alkylamino and/or methylenedioxy, or 3-indolyl, and their physiologically acceptable salts.

Those compounds of the formula I in which n is 1, $R^1$ denotes hydrogen, allyl, vinyl or an optionally protected side chain of a naturally occurring α-aminoacid, and R, $R^2$, Y, Z and X have the previous meanings, are preferred, in particular those compounds of the formula I in which n denotes 1, R denotes hydrogen, $R^1$ denotes methyl, the optionally acylated side chain of lysine or the O-$(C_1-C_6)$-alkylated side chain of tyrosine, $R^2$ denotes hydrogen, methyl, ethyl, benzyl or tert.-butyl, X denotes phenyl or phenyl which is monosubstituted or disubstituted by fluorine and/or chlorine, Y denotes hydrogen or hydroxyl, Z denotes hydrogen, or Y and Z together denote oxygen.

Particularly preferred compounds which may be mentioned are:

N-(1-S-carboethoxy-3-phenylpropyl)-S-alanyl-cis-2-azabicyclo[3.1.0]hexane-endo-3-S-carboxylic acid, N-(1-S-carboxy-3-phenylpropyl)-S-alanyl-cis-2-azobicyclo[3.1.0]hexane-endo-3-S-carboxylic acid, N-(1-S-carboethoxy-3-phenylpropyl)-S-lysyl-cis-2-azabicyclo[3.1.0]hexane-endo-3-S-carboxylic acid, N-(1-S-carboxy-3-phenylpropyl)-S-lysyl-cis-2-azabicyclo[3.1.0]hexane-endo-3-S-carboxylic acid, N-(1-S-carboethoxy-3-phenylpropyl)-O-ethyl-S-tyrosyl-cis2-azabicyclo[3.1.0]hexane-endo-3-S-carboxylic acid, N-(1-S-carboethoxy-3-phenylpropyl)-O-methyl-S-tyrosyl- cis-2-azabicyclo[3.1.0]hexane-endo-3-S-carboxylic acid, N-(1-S-carboethoxy-3-phenylpropyl)-S-alanyl-cis-2-azabicyclo[3.1.0]hexane-exo-3-S-carboxylic acid, N-(1-S-carboxy-3-phenylpropyl)-S-alanyl-cis-2-azabicyclo- [3.1.0]hexane-exo-3-S-carboxylic acid, N-(1-S-carboethoxy-3-phenylpropyl)-S-lysyl-cis-2-azabicyclo[3.1.0]hexane-exo-3-S-carboxylic acid, N-(1-S-carboxy-3-phenylpropyl)-S-lysyl-cis-2-azabicyclo[3.1.0]hexane-exo-3-S-carboxylic acid, N-(1-S-carboethoxy-3-phenylpropyl)-O-ethyl-S-tyrosyl-cis-2-azabicyclo[3.1.0]hexane-exo-3-S-carboxylic acid and N-(1-S-carboethoxy-3-phenylpropyl)-O-methyl-S-tyrosyl-cis-2-azabicyclo[3.1.0]hexane-exo-3-S-carboxylic acid.

Particularly suitable salts are alkali metal and alkaline earth metal salts, salts with physiologically tolerated amines, and salts with inorganic or organic acids, such as, for example, HCl, HBr, $H_2SO_4$, maleic acid, fumaric acid or tartaric acid.

In this context as in the following, aryl is to be understood to be optionally substituted phenyl, naphthyl or biphenylyl, but particularly phenyl. Alkyl can be straight-chain or branched. Acylamino is to be understood to be in particular $(C_1-C_6)$-alkanoylamino, Boc-amino or benzoylamino.

A monocyclic or bicyclic heterocyclic radical having 5 to 7 or 8 to 10 ring atoms respectively, 1 or 2 of these ring atoms being sulfur or oxygen atoms and/or 1 to 4 of these ring atoms being nitrogen atoms, is understood to include, for example, thienyl, benzo[b]thienyl, furyl, pyranyl, benzofuryl, pyrrolyl, imidazolyl, pyrazolyl, pyridyl, pyrimidinyl, pyridazinyl, indazolyl, isoindolyl, indolyl, purinyl, quinolizinyl, isoquinolinyl, phthalazinyl, naphthyridinyl, quinoxalinyl, quinazolyl, cinnolinyl, pteridinyl, oxazolyl, isoxazolyl, thiazolyl or isothiazolyl. These radicals can also be partially or completed hydrogenated.

Naturally occurring α-aminoacids are described in, for example, Houben-Weyl, Volumes XV/1 and XV/2.

If $R^1$ represents a protected side chain of a naturally occurring α-aminoacid, such as, for example, protected Ser, Thr, Asp, Asn, Glu, Gln, Arg, Lys, Hyl, Cys, Orn, Cit, Tyr, Trp, His or Hyp, the preferred protective groups are those customary in peptide chemistry (cf. Houben-Weyl, Volumes XV/1 and XV/2). In the case where $R^1$ denotes the protected side chain of lysine, the known amino protective groups, but particularly $(C_1-C_6)$-alkanoyl, are preferred. In the case where $R^1$ denotes the protected side chain of tyrosine, the ether protective group on the oxygen, in particular $(C_1-C_6)$-alkyl, is preferred; particularly preferred protective groups are methyl and ethyl.

Compounds of the formula I have chiral carbon atoms. The invention relates to both the R and the S configurations at all centers of asymmetry. Thus the compounds of the formula I can exist as optical isomers, as diastereomers, as racemates or as mixtures of these. However, those compounds of the formula I in which the carbon atom 3 in the bicyclic ring system as well as the carbon atoms in the side chain labelled with an asterisk (*) have the S configuration are preferred, with the exception that the R configuration of this center is preferred when $(NH-CHR^1-CO)=Cys$.

In addition, the invention relates to a process for the preparation of the compounds of the formula I which comprises reacting, by methods of amide formation known in peptide chemistry, a compound of the formula II, in which n, $R^1$, $R^2$, X, Y and Z have the previously mentioned meanings, with the exception of that of $R^2$=hydrogen, with a compound of the formulae IIIa or IIIb, or the mirror image or the racemate, in which W denotes a group esterifying carboxyl, such as $(C_1-C_6)$-alkyl or $(C_7-C_8)$-aralkyl, preferably tert.-butyl or benzyl, and subsequently liberating the compounds of type I with R=hydrogen by hydrogenation or treatment with acid and/or base.

Diastereomers of the formula I can be separated from one another by, for example, crystallization or chromatography.

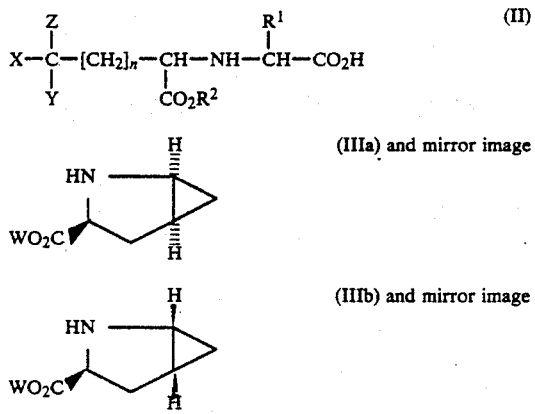

Further synthetic processes for the preparation of the compounds of the formula I in which Y and Z together denote oxygen entail reating, in a known manner in a Michael reaction (Organikum, 6th Edition, page 492, 1967), a compound of the formula IV

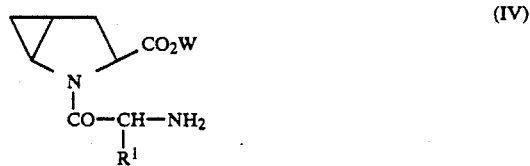

in which $R^1$ has the meaning as in formula I, and W has the meaning as in formulae IIIa and b, with a compound of the formula V

in which $R^2$ and X have the meanings as in formula I, and, where appropriate, splitting off the radical W and-/or the radical $R^2$ as described above, or reacting, in a known manner in a Mannich reaction (Bull. Soc. Chim. France 1973, page 625), a compound of the abovementioned formula IV with a compound of the general formula VI, in which $R^2$ has the meaning as in formula I, and with a compound of the general formula VII

in which X has the meaning as in formula I, and then, where appropriate, splitting off the radical W and/or the radical $R^2$ as described above with formation of the free carboxyl groups.

In addition, it is also possible to prepare compounds of the formula I with Y and Z each being hydrogen in a manner such that the compound of the abovementioned formula IV is reacted, in accordance with the procedure described in J. Amer. Chem. Soc. 93, 2897 (1971), with a compound of the formula VIII

in which $R^2$ and X have the meanings as in formula I, reducing the resulting Schiff's bases and then, where appropriate, splitting off the radical W and/or the radical $R^2$ as described above with formation of the free carboxyl groups. The reduction of the Schiff's bases can be carried out electrolytically or using reducing agents such as, for example, sodium borohydride or sodium cyanoborohydride.

Compounds of the formula I with Y being hydroxyl and Z being hydrogen can also be obtained by, for example, reducing a compound I, by Y and Z together being oxygen, which is obtained with the above procedures. This reduction can be carried out with a reducing agent, such as sodium borohydride and other complex boronates or, for example, borane-amine complexes.

Compounds of the formula I in which R represents hydrogen can, where appropriate, be converted by methods known per se into their esters of the formula I in which R denotes $(C_1$ to $C_6)$-alkyl or $(C_7$ to $C_9)$-aralkyl.

The reaction of a compound of the formula II with a compound of the formula III to prepare a compound of the formula I is carried out in accordance with a condensation reaction known in peptide chemistry, the condensing agents added being, for example, dicyclohexylcarbodiimide and 1-hydroxybenzotriazole. When subsequently splitting off the radical W with acid, the acids which are preferably employed are trifluoroacetic acid or hydrogen chloride.

Compounds of the formula II have already been proposed. Those with X being phenyl, Y being H, Z being H, $R^1$ being $CH_3$ and $R^2$ being $CH_3$ or $C_2H_5$ are known (for example from European Patent No. 0,037,231) and are accessible by various routes. The benzyl esters ($R^2$=benzyl) can be prepared analogously.

The Mannich reaction of acetophenones of the formula IXa, in which X represents aryl which is optionally substituted as previously, with glyoxylic esters and α-aminoacid esters leads to compounds of the formula II in which n denotes 1 and Y and Z together denote oxygen (formula IX). In formula IX, W' denotes a radical which can be split off by hydrogenolysis, or by base or acid, preferably benzyl or tert.-butyl, and X, where appropriate, represents the meanings defined previously.

However, in the case of the benzyl ester (W'=benzyl), R² may not be benzyl. On hydrogenolysis of these compounds with Pd, compounds of the formula II in which Y and Z are hydrogen are produced.

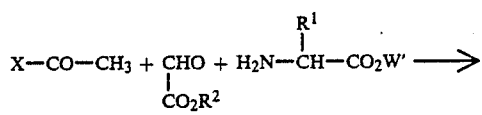

(IXa)

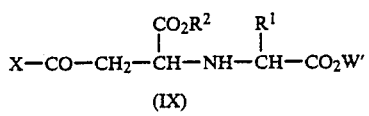

(IX)

Compounds of the formula II in which Y and Z together denote oxygen can likewise be obtained in high yields by Michael addition of appropriate acylacrylic esters and α-aminoacid esters. Ester cleavage leads to the same products as does the Mannich reaction.

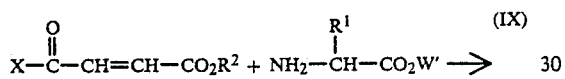

(IX)

The amount of the diastereomers having the preferred S,S configuration produced on using esters of L-aminoacids predominates, and they can be obtained by crystallization or chromatographic separation of the esters on silica gel.

The compounds of the abovementioned formula IV used as starting materials for the preparation of the compounds of the formula I are obtained from the compounds of the abovementioned formulae IIIa or b or the mirror images by reaction, by known procedures, with an N-protected 2-aminocarboxylic acid of the formula X

in which V is a protective group and R¹ has the abovementioned meaning. An example of a suitable protective group V, which is split off again after reaction is complete, is tert.-butoxycarbonyl.

The invention also relates to compounds of the formulae IIIa and IIIb and their mirror images in which W denotes hydrogen or a group esterifying carboxyl, preferably (C₁ to C₆)-alkyl or (C₇ or C₈)-aralkyl, and to a process for their preparation which comprises rearranging compounds of the formula XI

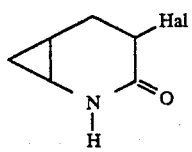

(XI)

in which Hal represents halogen, preferably chlorine or bromine, in the presence of a base, and, where appropriate, converting, in a manner known per se, the resulting compounds of the formulae IIIa or IIIb (W=hydrogen) and/or their mirror images into the abovementioned esters.

Compounds of the general formula XI can be prepared by converting a compound of the formula XII (Limasset et al., Bull. Soc. Chim. France 1969, 3981).

(XII)

into its oxime, reacting the latter in a Beckmann rearrangement, for example in analogy to Helv. Chim. Acta 46, 1190 (1963) to give a compound of the formula XIII

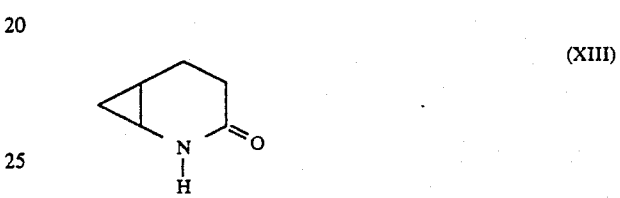

(XIII)

halogenating the latter to give a compound of the formula XIV

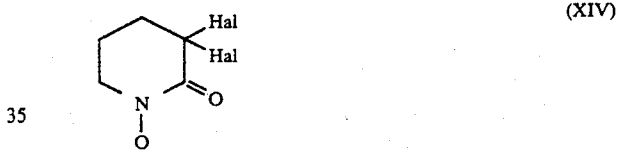

(XIV)

in which Hal denotes a halogen atom, preferably chlorine or bromine, and catalytically reducing the latter to give compounds of the formula XI.

The conversion of the ketone XII into the corresponding oxime is usually carried out in an aqueous-alcoholic medium with excess hydroxylamine hydrochloride, the free acid being neutralized with sodium carbonate or sodium acetate. In place of hydroxylamine, it is also possible to use sodium hydroxylamine-N,N-disulfonate (Org. Synth. 3 [1923] 61) or the sodium salt of hydroxylamine-N-monosulfonic acid (J. Amer. Chem. Soc. 46 [1924] 1290).

Reaction of the ketone XII with hydroxylamine-O-sulfonic acid in a concentrated organic acid, preferably formic acid, has proved to be particularly advantageous, the oxime being formed in situ and rearranged, without isolation, into the compound XIII, which is produced together with its isomer of the formula XIIIa.

(XIIIa)

Examples of suitable halogenating agents are inorganic acid halides, such as PCl₅, SO₂Cl₂, POCl₃, SOCl₂ or PBr₃, or halogens, such as bromine or chlorine. It is advantageous to use PCl₅ or POCl₃ combined with SO₂Cl₂ in an organic solvent. An imide halide is initially formed as an intermediate and reacts with the halogenating agents mentioned and then reacts further by hydrolysis under basic conditions, preferably with aqueous alkali metal carbonate, to give a compound of the formula XIV.

The compounds of the formula XIV are subsequently catalytically reduced in a polar protic solvent, such as, for example, an alcohol, preferably ethanol, or a carboxylic acid, such as, for example, acetic acid, with the addition of an acid acceptor, such as, for example, sodium acetate or triethylamine, to give a compound of the formula XI in which Hal has the abovementioned meaning. Examples of suitable catalysts are Raney nickel, or palladium or platinum on animal charcoal. Compounds of the formula XI can also be prepared directly or as mixtures with compounds of the formula XIV by halogenation of the compounds of the formula XIII using smaller amounts of the abovementioned halogenating agents.

Compounds of the formula XI are reacted in accordance with the known Favorskii reaction in the presence of a base to give the compounds of the formulae IIIa or b with W being hydrogen, and the latter are esterified where appropriate. The abovementioned Favorskii reaction is carried out in an alcoholic solvent such as methanol, ethanol or tert.-butanol or in water or in mixtures of these, at temperatures in the range from 20° to 140° C., preferably between 60° and 100° C. The bases which are advantageously employed are alkali metal or alkaline earth metal hydroxides, such as sodium, potassium or barium hydroxide or alkali metal alcoholates, such as, for example, sodium methylate or potassium tert.-butanolate.

The compounds of the formula IIIa and IIIb or their mirror images which are obtained in accordance with the procedure described above result as mixtures of stereoisomers, and these can be separated from one another by, for example, recrystallization or chromatography. It may be necessary, where appropriate, for the mixtures to be appropriately derivatized in order for the stereoisomers then to be separated from one another by recrystallization or chromatography.

Racemic mixtures of compounds of the formulae IIIa and IIIb can be employed as such in the further syntheses described above. However, if desired, they can also be separated into the enantiomers before further reactions by the known methods of racemate resolution (cf. for example, Quart. Rev. 25 (1971) 323 ff.).

If the compounds of the formula I result as racemates, these can also be resolved into their enantiomers or separated by chromatography by the customary methods, such as, for example, via salt formation with optically active bases or acids.

When R is hydrogen, the compounds of the formula I according to the invention exist as internal salts. Since they are amphoteric compounds, they can form salts with acids or bases. These salts are prepared in a customary manner by reaction with one equivalent of acid or base.

The compounds of the formula I and their salts have a long-lasting and strong hypotensive effect. They are potent inhibitors of angiotensin converting enzyme (ACE inhibitors) and can be employed to control hypertension of a variety of etiologies. It is also possible to combine them with other compounds having hypotensive, vasodilator or diuretic activity. Typical representatives of these classes of active compounds are described in, for example, Erhardt-Ruschig, Arzneimittel (Drugs), 2nd Edition, Weinheim, 1972. They can be administered intravenously, subcutaneously or orally. The dosage on oral administration is 1-100 mg, preferably 1-50, in particular 1-30 mg, per single dose for an adult of normal weight. This corresponds to about 13-1,300 μg/kg/day, preferably 13-650 μg/kg/day, in particular 13-400 μg/k/day. The dose can also be increased in severe cases, since toxic properties have not hitherto been observed. It is also possible to reduce the dose, and this is particularly appropriate when diuretics are administered concurrently.

The compounds according to the invention can be administered orally or parenterally in appropriate pharmaceutical formulations. For a form for oral use, the active compounds are mixed with the additives customary for this purpose, such as vehicles, stabilizers or inert diluents, and converted by customary methods into suitable forms for administration, such as tablets, coated tablets, hard gelatin capsules, aqueous, alcoholic or oily suspensions or aqueous, alcoholic or oily solutions. Examples of inert vehicles which can be used are gum arabic, magnesium carbonate, potassium phosphate, lactose, glucose or starch, in particular corn starch. For this purpose, the preparation can be carried out either as dry or as moist granules. Examples of suitable oily vehicles or solvents are vegetable and animal oils, such as sunflower oil or fish liver oil.

For subcutaneous or intravenous administration, the active compounds or their physiologically tolerated salts are converted into solutions, suspensions or emulsions with, if desired, the substances customary for this purpose, such as solubilizers, emulsifiers or other auxiliaries. Examples of suitable solvents for the new active compounds and the corresponding physiologically tolerated salts are: water, physiological salines or alcohols, for example ethanol, propanediol or glycerol, but also sugar solutions, such as glucose or mannitol solutions, or a mixture of the various solvents mentioned.

The examples which follow are intended to illustrate the procedures according to the invention without restricting the invention to the substances mentioned here as representatives.

The ¹H NMR data are δ values.

EXAMPLE I

N-(1-S-carboethoxy-3-phenylpropyl)-S-alanyl-cis-2-azabicyclo[3.1.0]hexane-3-carboxylic acid hydrochloride (1) Cis-2-azabicyclo[4.1.0]-3-oxoheptane 1 g of cis-bicyclo[3.1.0]-2-oxohexane are dissolved in 10 ml of 97% strength formic acid. While cooling in ice, 1.8 g of hydroxylamine-0-sulfonic acid in 5 ml of 97% strength formic acid are added, and the mixture is then brought to reflux temperature for 45 minutes. After cooling, the mixture is poured on to ice, neutralized with solid NaHCO₃ and extracted with ethyl acetate. After drying and evaporating, a residue of 1 g of oil remains.

(2) Cis-2-azabicyclo[4.1.0]-3-oxo-4-dichloroheptane 11 g of the crude product obtained according to Example I (1) are dissolved in 250 ml of dichloroethane. While cooling in ice, 20.8 g of phosphorus pentachloride are introduced. The mixture is stirred at room temperature for 30 minutes. Then, while cooling in ice, 17 ml of sulfuryl chloride are added dropwise, and the mixture is stirred under nitrogen at room temperature for 1 hour and at 60° C. (bath temperature) for 5 hours. After cooling, 200 g of ice are added, and the mixture is neutralized with solid sodium carbonate, the dichloroethane phase is separated off, and the aqueous phase is extracted with methylene chloride. The organic phases are dried, evaporated, and the residue (20 g) is chromatographed on silica gel using methylene chloride/ethyl acetate 19:1 as eluting agent.

Yield: 4.2 g. Melting point: 174°–175° C.

(3) Cis-2-azabicyclo[4.1.0]-3-oxo-4-chloroheptane 3.0 g of I(2) are dissolved in ethanol, 2.8 ml of triethylamine and 2.5 g of Raney nickel are added and the mixture is hydrogenated for 20 min. The catalyst is removed by filtration with suction, the filtrate is evaporated and the residue is chromatographed on silica gel using methylene chloride and ethyl acetate 19:1 as the eluting agent.

Yield: 1.8 g.

Analysis: $C_8H_8NOCl$: calculated: 49.5 5.5 9.6 24.3. Found 49.8 5.2 9.3 23.9.

(4a) Cis-2-azabicyclo[3.1.0]hexane-3-carboxylic acid 1.6 g of I(3) are suspended in 55 ml of water, and 4.0 g of $Ba(OH)_2.8H_2O$ are added. After refluxing for 1 hour, the pH is adjusted to 2.5 with 2 N sulfuric acid, the precipitate is filtered off with suction, and the aqueous solution is adjusted to pH 6, evaporated to dryness, ethanol and methylene chloride are added, and the precipitate is filtered off with suction, the solution is concentrated and ethyl acetate is added to the residue. Yield 1.5 g of colorless solid product.

$^1$H NMR/60 MHz, $D_2O$: 0.4–1.2 (m, 2 H); 1.5–2.9 (m, 3 H); 3.1–4.4 (m, 2 H)

(4b) Cis-2-azabicyclo[3.1.0]hexane-endo/exo-3-carboxylic acid

The product obtained in Example I(4a) comprises a mixture of cis-endo and cis-exo. After derivatization to give the benzyl ester followed by N-acylation with benzyl chloroformate, this product can be separated into the cis-endo and the cis-exo derivatives by silica gel chromatography. The racemic cis-endo and cis-exo aminoacids are obtained by subsequent hydrogenation with Pd/C (10%) as the catalyst.

$^1$H NMR of the cis-exo-2-azabicyclo[3.1.0]hexane-3-carboxylic acid. (270 MHz, $D_2O$): 0.8–0.93 (m, 2 H); 1.8–1.92 (m, 1 H); 2.1–2.24 (m, 1 H); 2.45–2.55 (qu, 1 H); 3.29–3.37 (m, 1 H); 3.78–3.88 (dd, 1 H).

$^1$H NMR of the cis-exo-2-azabicyclo[3.1.0]hexane-3-carboxylic acid. (270 MHz, $D_2O$): 0.56–0.66 (m, 1 H); 1.87–0.99 (split qu, 1 H) 1.79–1.9 (m, 1 H); 2.32–2.41 (m, 1 H); 2.48–2.62 (m, 1 H); 3.30–3.39 (m, 1 H) 4.26–4.35 (split d, 1 H).

The diastereomerically pure products or the mixture can be employed in the subsequent reactions.

(5a) Benzyl cis-2-azabicyclo[3.1.0]hexane-endo/exo-3-carboxylate 1.22 ml of thionyl chloride are added dropwise, at −15° C., to 30 ml of benzyl alcohol. Then, at −10° C., 1.5 g of the cis-endo/exo-aminoacid mixture prepared in Example I(4a) are introduced. After a reaction time of 24 hours at room temperature, the mixture is diluted with ether and extracted by stirring with water, cooling in ice. The aqueous solution is neutralized with NaHCO$_3$ and extracted with ether/methylene chloride which, after drying, is evaporated. Residue 2.2 g of oil.

$R_f$: 0.65 (silica gel, methylene chloride, methanol, glacial acetic acid, water 20:10:2:2, ninhydrin stain).

(5b) Benzyl cis-2-azabicyclo[3.1.0]hexane-exo-3-carboxylate

This compound is obtained by reacting the cis-exo-aminoacid prepared in Example I(4b) with benzyl alcohol and thionyl chloride by the process indicated in Example I(5a).

$R_f$: 0.62 (silica gel, methylene chloride, methanol, glacial acetic acid, water 20:10:2:2, ninhydrin stain)

(5c) Benzyl cis-2-azabicyclo[3.1.0]hexane-endo-3-carboxylate

This compound is obtained by reacting the cis-endo-aminoacid prepared in Example I(4b) with benzyl alcohol and thionyl chloride by the process indicated in Example I(5a).

$R_f$ 0.69 (silica gel, methylene chloride, methanol, glacial acetic acid, water 20:10:2:2, ninhydrin stain).

(6) Benzyl N-(1-S-carboxoethoxy-3-phenylpropyl)-S-alanyl-cis-2-azabicyclo[3.1.0]hexane-exo/endo-3-carboxylate 2.0 g of the benzyl ester prepared according to Example I(5a) are brought to reaction with 1.4 g of hydroxybenzotriazole (HOBt), 1.76 g of dicyclohexylcarbodiimide and 2.2 g of N-(1-S-carboethoxy-3-phenylpropyl)-S-alanine in 28 ml of dimethylformamide. After stirring at room temperature for 10 hours, the precipitated dicyclohexylurea is filtered off with suction, the filtrate is concentrated, the residue is taken up in methylene chloride and this solution is extracted 2× with saturated NaHCO$_3$ solution. The organic phase is dried, concentrated and 5.4 g of the mixture of cis-exo and cis-endo diastereomers are obtained.

(7) Benzyl N-(1-S-carboethoxy-3-phenylpropyl)-S-alanyl-cis-2-azabicyclo[3.1.0]hexane-endo-3-S-carboxylate (isomer 1)

The crude product obtained in Example I(6) is chromatographed on silica gel using cyclohexane/ethyl acetate in the ratio 1.5:1. The isomer which is eluted first is the S,S,S-cis-endo compound.

$R_f$: 0.24 (silica gel, cyclohexane/ethyl acetate 1:1).

$^1$H NMR (CDCl$_3$): 0.6–3.0 (m 13 H); 3.2–3.9 (m 4 H); 3.95–4.4 (q, 4 H); 4.8–5.0 (doublet of doublets, 1 H) 5.15 (s, 2 H); 7.25 (s, 5 H); 7.35 (s, 5 H).

(8) Benzyl N-(1-S-carboethoxy-3-phenylpropyl)-S-alanyl-cis-azabicyclo[3.1.0]hexane-endo-3-R-carboxylate (isomer 2)

The crude product obtained in Example I(6) is chromatographed on a column of silica gel using cyclohexane ethyl acetate in a ratio 1.5:1. The isomer which is eluted fourth is the cis-endo-S,S,R compound.

$R_f$: 0.09 (silica gel, cyclohexane/ethyl acetate 1:1).

(9) Benzyl N-(1-S-carboethoxy-3-phenylpropyl)-S-alanyl-cis-2-azabicyclo[3.1.0]hexane-exo-3-S-carboxylate (isomer 3)

The crude product obtained in Example I(6) is chromatographed on a silica gel column using cyclohexane/ethyl acetate in the ratio 1.5:1. The isomer which is eluted second is the cis-exo-S,S,S compound.

$R_f$: 0.20 (silica gel, cyclohexane/ethyl acetate 1:1).

(10) Benzyl N-(1-S-carboethoxy-3-phenylpropyl)-S-alanyl-cis-2-azabicyclo[3.1.0]-hexane-exo-3-R-carboxylate (isomer 4)

The crude product obtained in Example I(6) is chromatographed on a silica gel column using cyclohexane/ethyl acetate in the ratio 1.5:1. The isomer which is eluted third is the cis-exo-S,S,R compound.

$R_f$: 0.14 (silica gel, cyclohexane/ethyl acetate 1:1).

(11) N-(1-S-Carboethoxy-3-phenylpropyl)-S-alanyl-cis-2-azabicyclo[3.1.0]hexane-3-carboxylic acid hydrochloride 1.0 g of the benzyl ester prepared in Example I(6) is dissolved as the mixture of diastereomers in 50 ml of ethanol. 100 mg of palladium on charcoal (10%) is added to this and hydrogenation is carried out at room temperature under atmospheric pressure. After filtering off the catalyst by suction, the ethanolic solution is evaporated, ethanolic hydrochloric acid is added to the remaining oil and the solvent is evaporated off. The residue is vigorously stirred with ethyl acetate, whereupon a colorless solid mixture of the diastereomeric exo/endo carboxylic acids (hydrochlorides) remains.

Yield: 0.7 g.

EXAMPLE II

N-(1-S-Carboethoxy-3-phenylpropyl)-S-alanyl-cis-2-azabicyclo[3.1.0]hexane-endo-3-S-carboxylic acid hydrochloride (isomer I)

0.2 g of the benzyl ester prepared in Example I(7) is subjected to catalytic removal of the benzyl group in analogy to Example I(11), and the product is converted into the hydrochloride.

Yield: 0.125 g.

$^1$H NMR (DMSO-$d_6$): 0.6–5.0 (m, 21 H); 7.3 (s, 5 H); 9.7 (very broad s).

EXAMPLE III

N-(1-S-Carboethoxy-3-phenylpropyl)-S-alanyl-cis-2-azabicyclo[3.1.0]hexane-endo-3-R-carboxylic acid hydrochloride (isomer 2)

0.22 g of the benzyl ester prepared in Example I(8) is subjected to catalytic removal of the benzyl group in analogy to Example 1(11), and the product is converted into the hydrochloride.

Yield: 0.13 g.

$^1$H NMR (DMSO-$d_6$): 0.5–5.1 (m, 21 H); 7.2 (s, 5 H); 10.1 (very broad s).

EXAMPLE IV

N-(1-S-Carboethoxy-3-phenylpropyl)-S-alanyl-cis-2-azabicyclo[3.1.0]hexane-exo-3-S-carboxylic acid hydrochloride (isomer 3)

0.27 g of the benzyl ester prepared in Example I(9) is subjected to catalytic removal of the benzyl group in analogy to Example I(11), and the product is converted into the hydrochloride.

Yield: 0.23 g.

$^1$H NMR (DMSO-$d_6$): 0.5–4.7 (m, 21 H); 7.3 (s, 5 H); 10.0 (very broad s).

EXAMPLE V

N-(1-S-Carboethoxy-3-phenylpropyl)-S-alanyl-cis-2-azabicyclo[3.1.0]hexane-exo-3-R-carboxylic acid hydrochloride (isomer 4)

0.3 g of the benzyl ester prepared in Example I(10) is subjected to catalytic removal of the benzyl group in analogy to Example I(11), and the product is converted into the hydrochloride.

Yield: 0.26 g.

$^1$H NMR (DMSO-$d_6$): 0.4–4.8 (m, 21 H); 7.3 (s, 5 H); 9.8 (very broad s).

EXAMPLE VI

N-(1-S-Carboxy-3-phenylpropyl)-S-alanyl-cis-2-azabicyclo[3.1.0]hexane-endo-3-S-carboxylic acid (isomer 1)

0.2 g of the ethyl ester from Example II is dissolved in 5 ml of water. The solution is basified with a 4 N aqueous solution of potassium hydroxide. It is left to stand at 0° C. overnight. After reaction has ended, the pH is adjusted to 5 with concentrated hydrochloric acid. The solution is applied to 20 ml of strongly acid ion exchanger (IR 120, H+ form), which is developed with water and eluted with water containing 2% of hydrin. The fractions containing the above compound are evaporated. The residue is treated 2× with toluene and the toluene is removed under reduced pressure. Ether is added to the residue.

Yield: 0.13 g.

$^1$H NMR ($D_2O$): 0.6–5.1 (m, 15 H); 7.3 (s, 5 H).

EXAMPLE VII

N-(1-S-Carboxy-3-phenylpropyl)-S-alanyl-cis-2-azabicyclo[3.1 0]hexane-exo-3-S-carboxylic acid (isomer 3)

0.2 g of the ethyl ester from Example IV is hydrolyzed and worked up in analogy to Example VI.

Yield: 0.12 g.

$^1$H NMR ($D_2O$): 0.4–4.8 (m, 16 H); 7.2 (s, 5 H).

We claim:

1. A compound of the formula I

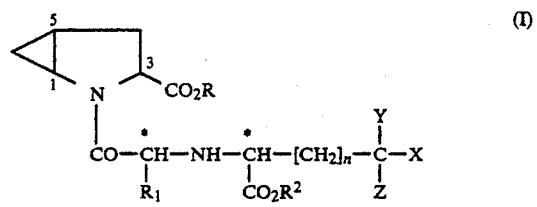

in which the hydrogen atoms at the bridgehead carbon atoms have the cis configuration with respect to one another, and the COOR group on carbon atom 3 is oriented exo or endo to the bicyclic ring system, and in which n denotes 0 or 1, R denotes hydrogen, ($C_1$–$C_6$)-alkyl, ($C_2$–$C_6$)-alkenyl or ($C_6$–$C_{12}$)-aryl-($C_1$–$C_4$)-alkyl, $R^1$ denotes hydrogen or ($C_1$ to $C_6$)-alkyl, which can optionally be substituted by amino, ($C_1$ to $C_6$)-acylamino or benzoylamino, ($C_2$ to $C_6$)-alkenyl, ($C_5$ to $C_9$)-cycloalkyl, ($C_5$ to $C_9$)-cycloalkenyl, ($C_5$ to $C_7$)-cyclo-alkyl-($C_1$ to $C_4$)-alkyl, ($C_6$ to $C_{12}$)-aryl or partially hydrogenated ($C_6$–$C_{12}$)-aryl, each of which can be substituted by ($C_1$ to $C_4$)-alkyl, ($C_1$ or $C_2$)-alkoxy or halogen, $(C_6-C_{12})$-aryl-$(C_1$ to $C_4)$-alkyl or $(C_7-C_{13})$- aroyl-$(C_1-C_2)$-alkyl, both of which can be substituted in the aryl radical as defined above, or an optionally protected side chain of a naturally occurring α-aminoacid $R^1$—CH(NH$_2$)—COOH, $R^2$ denotes hydrogen, $(C_1-C_6)$-alkyl, $(C_2-C_6)$-alkenyl or $(C_6-C_{12})$-aryl-$(C_1-C_4)$-alkyl, Y denotes hydrogen or hydroxyl, Z denotes hydrogen, or Y and Z together denote oxygen, and X denotes $(C_1-C_6)$-alkyl, $(C_2-C_6)$-alkenyl, (C cycloalkyl, $(C_6-C_{12})$-aryl, which can be monosubstituted, disubstituted or trisubstituted by $(C_1-C_4)$-alkyl, $(C_1-C_4)$-alkoxy, hydroxyl, halogen, nitro, amino, $(C_1-C_4)$-alkylamino, di-$(C_1-C_4)$-alkylamino and/or methylenedioxy, or 3-indolyl,
and its physiologically acceptable salts.

2. A compound of the formula I as claimed in claim 1, wherein the carbon atom in position 3 of the bicyclic ring system and the carbon atoms in the side chain labelled with an asterisk each have the S configuration.

3. A compound of the formula I as claimed in claim 1, in which n is 1, $R^1$ denotes hydrogen, allyl, vinyl or an optionally protected side chain of a naturally occurring α-aminoacid, and R, $R^2$, Y, Z and X have the meanings defined in claim 1.

4. A compound of the formula I according to claim 1, in which n denotes 1,

R denotes hydrogen, $R^1$ denotes methyl, the optionally acylated side chain of lysine or the O-$(C_1-C_6)$-alkylated side chain of tyrosine, $R^2$ denotes hydrogen, methyl, ethyl, benzyl or tert.-butyl, X denotes phenyl or phenyl which is monosubstituted or disubstituted by fluorine and/or chlorine, Y denotes hydrogen or hydroxyl, Z denotes hydrogen, or Y and Z together denote oxygen.

5. A compound of the formula I according to claim 1 which is N-(1-S-carboethoxy-3--phenylpropyl)-S-alanyl-cis-2-azabicyclo[3.1.0]hexane-endo-3-S-carboxylic acid.

6. A compound of the formula I according to claim 1 which is N-(1-S-carboxy-3-phenylpropyl)-S-alanyl-cis-2-azabicyclo[3.1.0]hexane-endo-3-carboxylic acid.

7. A compound of the formula I according to claim 1 which is N-(1-S-carboethoxy-3-phenylpropyl)-S-alanyl-cis-2-azabicyclo[3.1.0]hexane-exo-3-S-carboxylic acid.

8. A compound of the formula I according to claim 1 which is N-(1-S-carboxy-3-phenylpropyl)-S-alanyl-cis-2-azabicyclo[3.1.0]hexane-exo-3-carboxylic acid.

9. A compound of the formula IIIa

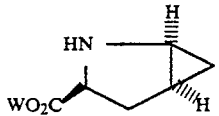

or IIIb,

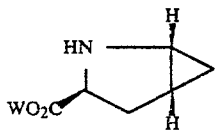

in which W denotes hydrogen or a group esterifying carboxyl, and the mixture of its stereoisomers.

10. A pharmaceutical composition comprising a hypotensively effective amount of a compound or a mixture of compounds according to claim 1 or a pharmaceutically acceptable salt thereof and a pharmaceutically acceptable carrier.

11. A method of treating hypertension by administering an effective amount of a compound according to claim 1 or a pharmaceutically acceptable salt thereof.

* * * * *